US00PP19220P2

(12) United States Plant Patent
Hannink

(10) Patent No.: US PP19,220 P2
(45) Date of Patent: Sep. 16, 2008

(54) ***CLEMATIS* PLANT NAMED 'SNOW BELLS'**

(50) Latin Name: *Clematis henryi*
Varietal Denomination: Snow Bells

(75) Inventor: Johannes Antonius Jozef Hannink, Drunen (NL)

(73) Assignee: Ruud Van Der Werf, Boskoop (NL)

( * ) Notice: Subject to any disclaimer, the term of this patent is extended or adjusted under 35 U.S.C. 154(b) by 0 days.

(21) Appl. No.: 11/805,303

(22) Filed: May 23, 2007

(51) Int. Cl.
*A01H 5/00* (2006.01)

(52) U.S. Cl. ..... Plt./228

(58) Field of Classification Search ..... None
See application file for complete search history.

*Primary Examiner*—Annette H Para
(74) *Attorney, Agent, or Firm*—Jondle & Associates, P.C.

(57) ABSTRACT

A *clematis* plant particularly distinguished by being floriferous and having light green-white to white flowers. In addition, the flowers are visible and not hidden behind the foliage and have a very strong and pleasant fragrance. The plant is evergreen and flowers in late winter.

2 Drawing Sheets

Genus and species: *Clematis henryi.*
Variety denomination: 'Snow Bells'.

BACKGROUND OF THE NEW PLANT

The present invention comprises a new and distinct cultivar of *Clematis,* botanically known as *Clematis henryi* and hereinafter referred to by the cultivar name 'Snow Bells'. The new cultivar originated from a hybridization made in 2002 in Drunen, The Netherlands. The female parent was an unnamed, individual plant of *Clematis henryi* (unpatented) having white flowers, while the male parent was an unnamed, individual plant of *Clematis henryi* having white flowers (unpatented).

The new cultivar was created in 2002 in Drunen, The Netherlands and has been asexually reproduced repeatedly by softwood cuttings in Boskoop, The Netherlands over a one-year period. The present invention has been found to retain its distinctive characteristics through successive asexual propagations.

Plant Breeder's Rights for this cultivar have been applied for with the European Union on Jan. 9, 2007.

SUMMARY OF THE INVENTION

The following are the most outstanding and distinguishing characteristics of the new cultivar when grown under normal horticultural practices in Drunen and Boskoop, The Netherlands.

1. Very floriferous with light green-white to white flowers;
2. Flowers in late winter;
3. The flowers are visible and not hidden behind the foliage;
4. The flowers have a very strong and pleasant fragrance; and
5. Is evergreen;

DESCRIPTION OF THE PHOTOGRAPHS

This new *clematis* plant is illustrated by the accompanying photographs which show overall plant habit including blooms, buds and foliage of the plant; the colors shown are as true as can be reasonably obtained by conventional photographic procedures. The photos are of two-year-old plants grown in a greenhouse in February.

DESCRIPTION OF THE NEW CULTIVAR

Figure 1:
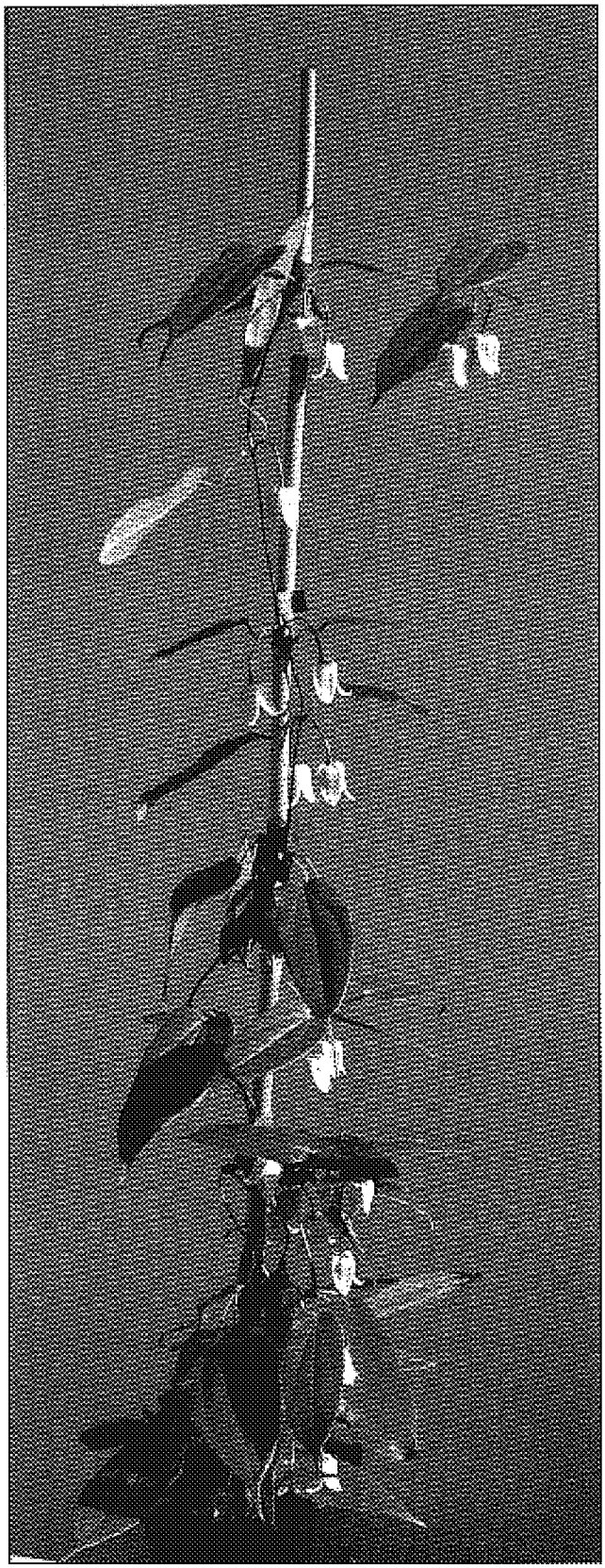
FIG. 1 shows the overall plant habit, including blooms, buds and foliage.
Figure 2:
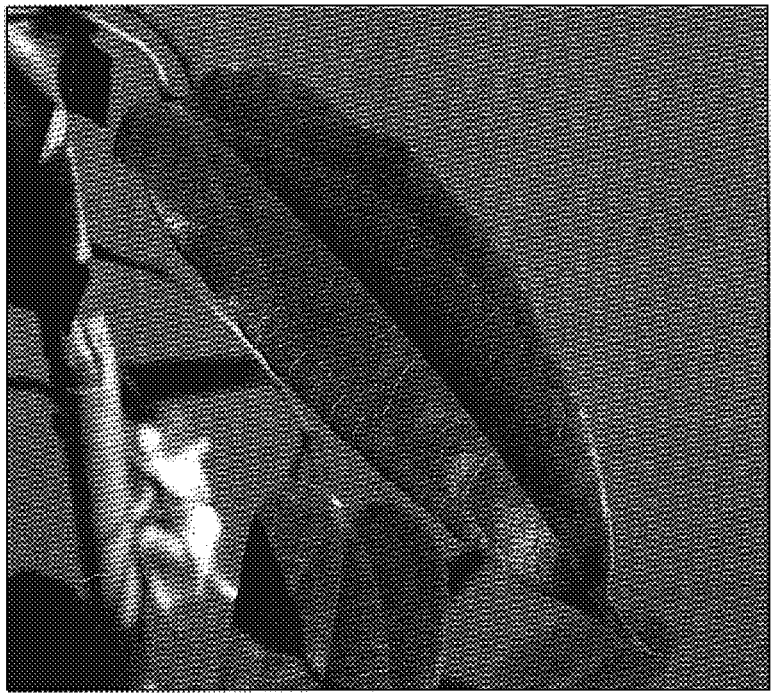
FIG. 2 shows a close-up of a mature leaf.
Figure 3:
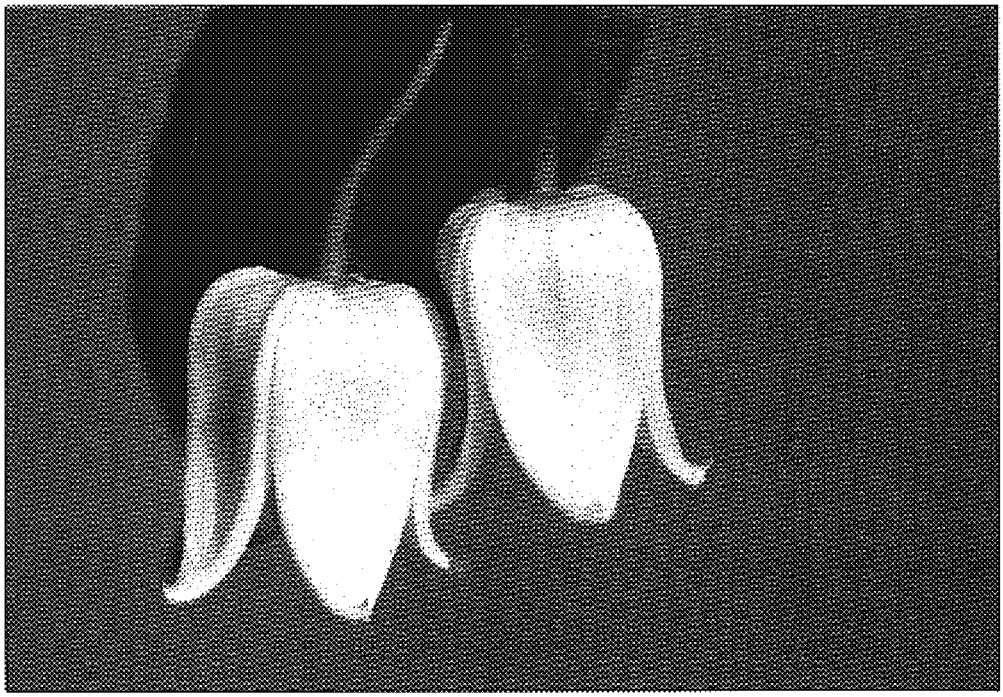
FIG. 3 shows a close-up of the mature flower.

The following detailed descriptions set forth the distinctive characteristics of 'Snow Bells'. The data which define these characteristics were collected from asexual reproductions carried out in Boskoop, The Netherlands. The plant history was taken on one-year-old un-pinched plants grown in 13-cm pots in a greenhouse in Boskoop, The Netherlands in February. The average daily temperatures ranged from 3° C. to 12° C. while the average night temperatures ranged from 0° C. to 7° C. Color readings were taken in the greenhouse under natural light. Color references are primarily to the R.H.S. Colour Chart of The Royal Horticultural Society of London (R.H.S.) (2001 edition).

DETAILED BOTANICAL DESCRIPTION

Classification:
- *Family.*—Ranunculaceae.
- *Botanical.—Clematis henryi.*
- *Common name.—Clematis.*

Parentage:
- *Female parent.*—An unnamed, individual plant of *Clematis henryi* (unpatented) having white flowers.
- *Male parent.*—An unnamed, individual plant of *Clematis henryi* having white flowers (unpatented).

Growth:
- *Form.*—Perennial vine.
- *Growth habit and vigor.*—Upright and climbing with moderate vigor.
- *Branching habit.*—Moderate, stems grow from the base.

*Height* (*measured from the top of the soil*).—78.4 cm.
*Width* (*horizontal plant diameter*).—26.3 cm.
*Time to produce a finished flowering plant.*—Approximately 14 months from an un-rooted cutting to a deliverable plant.
*Outdoor plant performance.*—Use in containers (13 cm or larger) and beds; pinching of the terminal apices not required but will enhance branching; tolerant to rain and wind.
*Growth rate.*—In the spring, approximately 15 cm per month.
*Temperature tolerances.*—High and low temperature tolerances unknown; tolerant to high temperatures of at least 35° C. and to low temperatures for USDA zone 8.
*Time to initiate root developments.*—21 days in the summer at 18° C.
*Time to produce a rooted cutting/young plant.*—21 days in the summer at 18° C.

Stems:
*Number of lateral branches per plant.*—4.
*Length.*—53.4 cm.
*Diameter.*—0.15 cm.
*Internode length.*—7.9 cm.
*Color.*—RHS 137A (green) while older bark is RHS 200D (brown).
*Appearance.*—Slightly glossy; lateral stems are slightly thickened at the nodes and 0.25 cm in diameter.
*Aspect.*—Rounded.
*Texture.*—Young stems are moderately pubescent while older stems are sparsely covered with very short hairs that are about 0.4 mm in length and closest to RHS 157D (light green-white).
*Strength.*—Strong.

Leaves:
*Arrangement.*—Opposite.
*Type.*—Single.
*Quantity of leaves per lateral branch.*—16 (8 pairs).
*Immature leaf.*—Color: Upper surface: RHS 143A (green). Lower surface: RHS 143B (green).
*Mature leaf.*—Color: Upper surface: Between RHS 137A and RHS 193A (green). Lower surface: RHS 137A and RHS 137B. Length: 11.2 cm. Width: 4.5 cm. Shape: Lanceolate to narrow-ovate. Apex: Apiculate. Base: Cordate to truncate. Margin: Finely serrate. Texture: Glossy and slightly leathery; sparsely covered with very short hairs on the upper surface and on the main and secondary veins of the lower surface; the hairs are 0.4 mm in length and closest to RHS 157D (light green-white). Venation: Pinnate with three conspicuous veins from the base. Venation color: Upper surface: RHS 137A (green). Lower surface: RHS 143A (green). Durability of foliage to environmental stresses: High.
*Petioles.*—Length: 3.0 cm. Diameter: 0.15 cm. Color: RHS 143A. Texture: Moderately glossy; sparsely covered with very short hairs; the hairs are 0.4 mm in length and closest to RHS 157D (light green-white).
*Tendrils.*—General: The petioles are clasping petioles — are used to attach itself.

Flower buds:
*Quantity of buds per lateral stem.*—13.
*Shape.*—Ovate.
*Length.*—1.8 cm.
*Diameter.*—1.1 cm.
*Color* (*at tight bud*).—RHS 145B (yellow-green) and darker, RHS 145A, near the petiole.
*Rate of opening.*—Approximately three days.

Flowers:
*Blooming habit.*—Plant blooms once per year in late winter, from February to March; approximately 75% of the flowers on a plant are open at a given time.
*Lastingness of the individual flowers on the plant.*—10 days.
*Quantity of flowers and buds on the plant at a given time.*—52.
*Arrangement and type.*—Axillary with terminal, solitary (single) flowers.
*Quantity of flowers per lateral stem.*—13.
*Fragrance.*—Present; a strong and very pleasant fresh acid to acidic sweet fragrance similar to *Daphne odora.*
*Aspect.*—Drooping.
*Shape.*—Campanulate.
*Diameter.*—2.6 cm.
*Depth* (*height*).—2.0 cm.
*Tepals.*—Arrangement: Rotate, 4-parted. Quantity of tepals per flower: 4. Appearance: Dull and smooth. Shape: Ovate. Apex: Acute. Base: Cuneate. Margin: Entire. Texture: Densely pubescent; hairs are very short, about 0.2 mm in length and RHS 155C (white) to RHS 157A (green-white). Length: 2.2 cm. Width: 1.2 cm. Color (when opening): Upper surface: RHS 145B (yellow-green) and RHS 145C (yellow-green). Lower surface: RHS 145B (yellow-green). Color (fully opened): Upper surface: RHS 155C (white) to RHS 157A (green-white) and slightly darker towards the tip, RHS 150D. Lower surface: RHS 145B (yellow-green) and lighter towards the tip, RHS 145C.
*Pedicels.*—Length: 3.2 cm. Diameter: 0.15 cm. Angle: Average of 90 degrees. Strength: Strong. Color: RHS 141B (green).

Reproductive organs:
*Stamens.*—55 per flower. Anther: Shape: Basifixed, linear. Length: 0.15 cm. Color: RHS 160C (greyed-yellow). Filament: General: Glands at the base of the filaments release a colorless sticky substance when the filaments are removed. Length: 1.2 cm. Color: RHS 157A (green-white) to RHS 150D (yellow-green). Pollen amount: Sparse. Pollen color: RHS 160C (greyed-yellow).
*Pistil quantity.*—75 per flower.
*Pistil length.*—1.3 cm.
*Stigma shape.*—Narrow conical.
*Stigma color.*—RHS 150D (yellow-green).
*Style length.*—1.2 cm.
*Style color.*—RHS 157A (green-white).
*Ovary color.*—RHS 157A (green-white).

Fruit/seed set: None observed.

Disease and insect resistance: Highly resistant to pests and diseases.

COMPARISON WITH PARENTAL AND COMMERCIAL CULTIVARS

'Snow Bells' differs from the female parent, an unnamed individual plant of *Clematis henryi* (unpatented) in that 'Snow Bells' is floriferous and has flowers with a strong fragrance, while the female parent is less floriferous and has flowers that are slightly fragrant.

'Snow Bells' differs from the male parent, an unnamed, individual plant of *Clematis henryi* (unpatented) in that 'Snow Bells' is floriferous and has flowers that are light green-white to white with a strong fragrance, while the male parent is less floriferous and has faintly fragrant flowers.

'Snow Bells' differs from the commercial *Clematis urophylla* 'Winter Beauty' (unpatented) in that 'Snow Bells' flowers in late winter and has simple leaves, while 'Winter Beauty' flowers in early winter and has ternate leaves. Additionally, 'Snow Bells' is floriferous and has flowers with a strong fragrance, while 'Winter Beauty' is less floriferous and has flowers with no fragrance.

I claim:

1. A new and distinct cultivar of *Clematis* plant as shown and described herein.

* * * * *